United States Patent
Park et al.

(10) Patent No.: US 9,504,450 B2
(45) Date of Patent: Nov. 29, 2016

(54) APPARATUS AND METHOD FOR COMBINING THREE DIMENSIONAL ULTRASOUND IMAGES

(71) Applicants: Samsung Electronics Co., Ltd., Suwon-si (KR); SAMSUNG LIFE PUBLIC WELFARE FOUNDATION, Seoul (KR)

(72) Inventors: Moon-Ho Park, Hwaseong-si (KR); Ye-Hoon Kim, Seoul (KR); Yeong-Kyeong Seong, Yongin-si (KR); Baek-Hwan Cho, Seoul (KR); Min Woo Lee, Seoul (KR)

(73) Assignees: Samsung Electronics Co., Ltd., Suwon-si (KR); Samsung Life and Welfare Foundation, Seoul (KR)

( * ) Notice: Subject to any disclaimer, the term of this patent is extended or adjusted under 35 U.S.C. 154(b) by 80 days.

(21) Appl. No.: 14/325,764

(22) Filed: Jul. 8, 2014

(65) Prior Publication Data

US 2015/0157298 A1    Jun. 11, 2015

(30) Foreign Application Priority Data

Dec. 11, 2013   (KR) .................. 10-2013-0154050

(51) Int. Cl.
*A61B 8/08* (2006.01)
*A61B 8/00* (2006.01)
*G06K 9/46* (2006.01)
*G06T 7/00* (2006.01)

(52) U.S. Cl.
CPC .............. *A61B 8/5253* (2013.01); *A61B 8/466* (2013.01); *A61B 8/5207* (2013.01); *G06K 9/46* (2013.01); *G06T 7/0028* (2013.01); *G06T 2207/10136* (2013.01); *G06T 2207/30048* (2013.01)

(58) Field of Classification Search
USPC .................................................. 382/128, 131
See application file for complete search history.

(56) References Cited

U.S. PATENT DOCUMENTS

| | | | |
|---|---|---|---|
| 6,947,584 B1 | 9/2005 | Avila et al. |
| 7,315,304 B2 | 1/2008 | Liang et al. |
| 7,657,073 B2 | 2/2010 | Sun et al. |
| 7,907,772 B2 | 3/2011 | Wang et al. |
| 2007/0073135 A1 | 3/2007 | Lee et al. |

(Continued)

FOREIGN PATENT DOCUMENTS

| | | |
|---|---|---|
| KR | 10-0420791 B1 | 3/2004 |
| KR | 10-2010-0096224 A | 9/2010 |
| KR | 10-1107478 B1 | 1/2012 |

*Primary Examiner* — Bhavesh Mehta
*Assistant Examiner* — Narek Zohrabyan
(74) *Attorney, Agent, or Firm* — Jefferson IP Law, LLP

(57) ABSTRACT

An apparatus and a method for combining three-dimensional ultrasound images are provide. The method involves obtaining a plurality of three-dimensional ultrasound image data that corresponds to a Region of Interest (ROI); detecting one or more landmarks, using a parameter for detection; outputting the detection result and receiving a response from a user; registering each of one or more selected landmarks as link information according to a received response from the user; and generating a combined three-dimensional ultrasound image by combining at least two pieces of three-dimensional ultrasound image data using at least one of the one or more selected landmarks registered as the link information, wherein the at least two pieces of three-dimensional ultrasound image data commonly comprise the at least one of the one or more selected landmarks.

20 Claims, 7 Drawing Sheets

(56) References Cited

U.S. PATENT DOCUMENTS

| | | |
|---|---|---|
| 2008/0279429 A1 | 11/2008 | Fradkin et al. |
| 2009/0012383 A1* | 1/2009 | Virtue ................... A61B 6/032 600/407 |
| 2010/0135544 A1 | 6/2010 | Mattiuzzi et al. |
| 2010/0152585 A1* | 6/2010 | Kim ........................ A61B 8/00 600/443 |
| 2010/0228122 A1 | 9/2010 | Keenan et al. |
| 2011/0028825 A1 | 2/2011 | Douglas et al. |
| 2011/0158491 A1* | 6/2011 | Markova ............... G06T 3/0081 382/128 |
| 2011/0178389 A1* | 7/2011 | Kumar ................... A61B 5/055 600/411 |
| 2012/0093383 A1* | 4/2012 | Claus ..................... A61B 6/032 382/131 |
| 2012/0172700 A1* | 7/2012 | Krishnan ............... A61B 6/032 600/407 |
| 2012/0183193 A1 | 7/2012 | Wels et al. |
| 2012/0189176 A1* | 7/2012 | Giger .................... G06K 9/6253 382/128 |
| 2015/0193962 A1* | 7/2015 | Ohuchi ................. A61B 6/4417 345/427 |
| 2016/0038121 A1* | 2/2016 | Waechter-Stehle .... A61B 8/085 600/443 |

* cited by examiner (a)

(b)

(c)
Classification Result: Benign
- Category: cyst
- Roundness: mildly lobulated
- Sharpness of margin: well-defined
- Presence of peripheral rim: absence
- Echogenicity: hypoechoic
- Homogeneity: homogeneous
  ... — 110

APPARATUS AND METHOD FOR COMBINING THREE DIMENSIONAL ULTRASOUND IMAGES

CROSS-REFERENCE TO RELATED APPLICATION(S)

This application claims the benefit under 35 USC 119(a) of Korean Patent Application No. 10-2013-0154050 filed on Dec. 11, 2013, in the Korean Intellectual Property Office, the entire disclosure of which is incorporated herein by references for all purposes.

BACKGROUND

1. Field

The following description relates to an apparatus and a method of combining three-dimensional (3D) ultrasound images in order to obtain a combined 3D ultrasound image.

2. Description of Related Art

Ultrasound imaging is a technology related to transmitting inaudible high frequency sound waves having a frequency between 20 kHz and 150 MHz into an object and visualizing the internal structure of the object based on the waves reflected off from the internal structure of the object. Ultrasound image diagnosis techniques are classified into various modes according to how an image is displayed to the user. For example, brightness mode (B-mode) image diagnosis technique displays two-dimensional gray images that are used for general ultrasound diagnosis. Furthermore, an ultrasonic phased array transducer has two-dimensionally arranged elements that are lineally arranged therein for generating two-dimensional images; such an ultrasonic phased array transducer may steer or focus an ultrasonic beam. As a result, information regarding different section layers is obtained, and a three-dimensional image can be obtained by combining information regarding the different slices into one image. In addition, a real-time three-dimensional image (or four-dimensional image) may be realized, if the slices are combined substantially in real time.

However, due to a limited spatial range for capturing an ultrasound image, it is almost impossible to fully capture a Region of Interest (ROI) by one scan. For this reason, the same ROI is scanned at different locations, and a plurality of ultrasound images that partially overlap with each other are obtained. To put it simply, for accurate and thorough diagnosis on an ROI, a plurality of ultrasound images are analyzed, and the analyzing of each of the ultrasound images that belongs to the same ROI and the bringing about of an integrated and accurate diagnosis result therefrom are complicated and require expertise.

For example, a method for combining three-dimensional ultrasound images including a plurality of different special areas may involve comparing all or some of the pixels of a plurality of slices included in the three-dimensional ultrasound images with reference to locations and directions of the pixels. In this example, all the pixels/voxels of the three-dimensional images are compared with each other in order to combine the images; thus, a large amount of computation must be performed, requiring the use of a high-performance computing device and the consumption of a long processing time for performing the computation. Further, in an example in which a method for combining three-dimensional images by extracting characteristic shapes from the images and comparing the extracted shapes with each other is applied, there may be instances in which no characteristic shape, too few characteristic shapes or too many characteristic shapes are found; thus, the process of image combination may turn into a challenge. In yet another example, a method of combining three dimensional images using specific anatomical features (for example, blood vessel and bone) may be used for image combination. In this case, it is hard to interconnect three-dimensional images if an anatomical feature does not exist in each of the three-dimensional images that are being combined.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a method for combining a plurality of three-dimensional ultrasound image data, involving: obtaining a plurality of three-dimensional ultrasound image data that corresponds to a Region of Interest (ROI); detecting one or more landmarks, using a parameter for detection, the one or more landmarks each comprising at least one feature distinct from surroundings thereof; outputting the detection result and receiving a response from a user; registering each of one or more selected landmarks as link information according to a received response from the user; and generating a combined three-dimensional ultrasound image by combining at least two pieces of three-dimensional ultrasound image data using at least one of the one or more selected landmarks registered as the link information, wherein the at least two pieces of three-dimensional ultrasound image data commonly include the at least one of the one or more selected landmarks.

The plurality of three-dimensional ultrasound image data may partially overlap with each other and may correspond to different locations of the ROI, and the detecting may comprise: performing diagnosis on each of the plurality of three-dimensional ultrasound image data using the parameter for detection, and detecting one or more landmarks based on the diagnosis, the one or more landmarks each having volume greater than a predetermined reference value.

The method may further involve: updating the parameter for detection; performing diagnosis on the combined three-dimensional ultrasound image data using the updated parameter for detection; and modifying the combined three-dimensional image data based on the diagnosis result.

The outputting of the detection result and the receiving of the response from the user may involve outputting one or more candidate landmarks as the detection result, and waiting to receive, as the response from the user, information that indicates one or more landmarks selected by the user from among the one or more candidate landmarks.

The outputting of the detection result and the receiving of the response from the user may involve: outputting one or more candidate landmarks as the detection result, and waiting to receive a modified parameter for detection as the response from the user; updating a parameter for detection based on the modified parameter for detection; and re-outputting one or more candidate landmarks after performing diagnosis on each of the plurality of three-dimensional ultrasound image data using the updated parameter for detection, and waiting to receive, as the response from the user, information that indicates one or more landmarks selected by the user from among the one or more candidate landmarks.

The outputting of the detection result and the receiving of the response from the user may involve: outputting, as the detection result, information indicating that no candidate landmark is detected, and waiting, as the response from the user, a new parameter for detection; updating the parameter for detection based on the new parameter for detection; and re-outputting one or more candidate landmarks after performing diagnosis on each of the plurality of three-dimensional ultrasound image data using the updated parameter for detection, and waiting, as the response from the user, information that indicates one or more landmark selected by the user from among the one or more candidate landmarks.

The parameter for detection may involve at least one of a classification result which indicates either benignity or malignancy, category, roundness, sharpness of margin, presence of peripheral rim, echogenicity, and homogeneity.

The parameter for detection may involve information that relates to at least one of an entire shape, texture of an outer surface and posture.

The parameter for detection may further involve link information that relates to at least one of anatomical features, such as a blood vessel and bone, which are located close to a landmark.

In another general aspect, an apparatus for combining three-dimensional ultrasound image includes: a processor configured to obtain a plurality of partially-overlapping three-dimensional ultrasound image data corresponding to different locations of a Region of Interest (ROI), and to detect from each of the plurality of three-dimensional ultrasound image data one or more landmarks using a parameter for detection, the one or more landmarks each comprising at least one feature distinct from surroundings thereof; an input/output device configured to output a detection result and to receive a response from a user, wherein the processor is configured to register the one or more selected landmarks as link information based on the received response, and to generate a combined three-dimensional ultrasound image by combining at least two pieces of three-dimensional ultrasound image data using at least one of the one or more selected landmarks registered as the link information, the at least two pieces of three-dimensional ultrasound image data commonly comprising the at least one of the one or more selected landmarks.

The plurality of three-dimensional ultrasound image data may partially overlap with each other and may correspond to different locations of the ROI, and the processor may be configured to perform diagnosis on each of the plurality of three-dimensional ultrasound image data using the parameter for detection and detects the one or more landmarks based on the diagnosis, the one or more landmarks each having volume greater than a predetermined reference value.

The processor may be further configured to perform diagnosis on the combined three-dimensional ultrasound image data using an updated parameter for detection and to modify the combined three-dimensional image data based on the diagnosis result.

The input/output device may be configured to output the detection result and to receive the response from the user by: outputting one or more candidate landmarks as the detection result, and waiting to receive, as the response from the user, information that indicates one or more landmarks selected by the user from the one or more candidate landmarks.

The input/output device may be configured to output the detection result and to receive the response from the user by: outputting one or more candidate landmarks as the detection result, and waiting to receive a modified parameter for detection as the response from the user, the parameter for detection being updated based on the altered parameter for detection, and re-outputting one and more candidate landmarks after performing diagnosis on the combined three-dimensional ultrasound image data using the updated parameter for detection, and waiting, as the response from the user, information that indicates one or more landmarks selected by the user from the one or more re-output candidate landmarks.

The input/output device may be configured to output the detection result and to receive the response from the user by: outputting the detection result indicating that no landmark is detected, and waiting to receive a new parameter for detection as the response from the user, the parameter for detection being updated based on the new parameter for detection, and outputting one or more candidate landmarks after re-performing diagnosis on the combined three-dimensional ultrasound image data using the updated parameter for detection, and waiting, as the response from the user, information that indicates one or more landmark selected by the user from among the one or more candidate landmarks.

The parameter for detection may include information relating to at least one of a classification result that indicates either benignity or malignancy, category, roundness, sharpness of margin, presence of peripheral rim, echogenicity, and homogeneity.

The parameter for detection may include at least one of shape, texture of outer surface and orientation.

The parameter for detection may further include link information relating to at least one of anatomical features, such as blood vessel and bone, which are close the landmark.

In another general aspect, there is provided a non-transitory computer readable medium storing instructions configured to cause a computing device to perform the above described method.

Other features and aspects will be apparent from the following detailed description, the drawings, and the claims.

Figure 1:
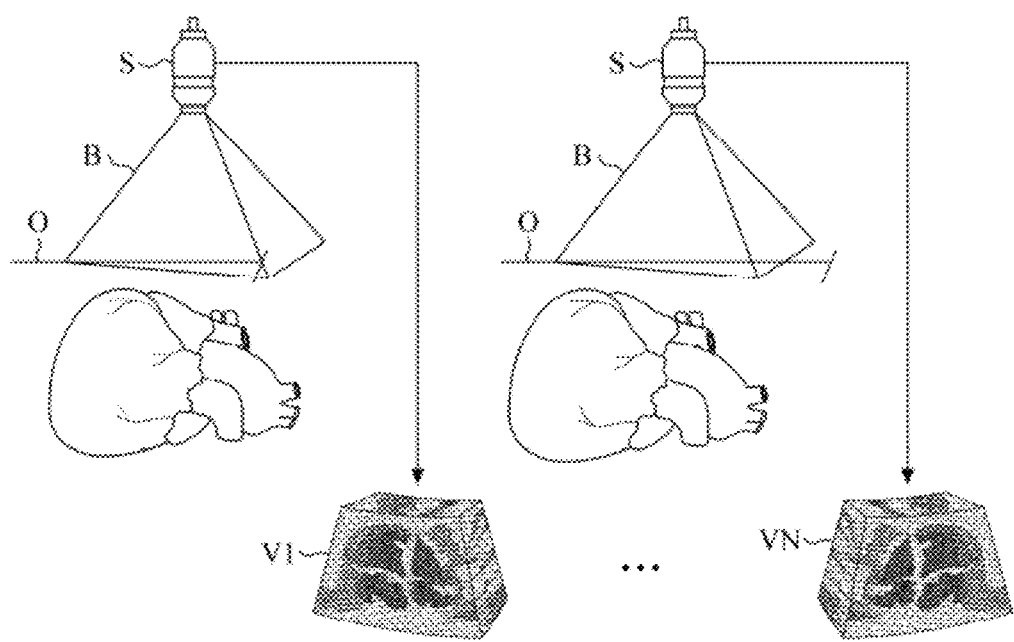
FIG. 1 is a diagram illustrating an example of an operation of obtaining three-dimensional ultrasound images that are used in a method for combining three-dimensional ultrasound images to obtain a combined three-dimensional ultrasound image.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Figure 6:
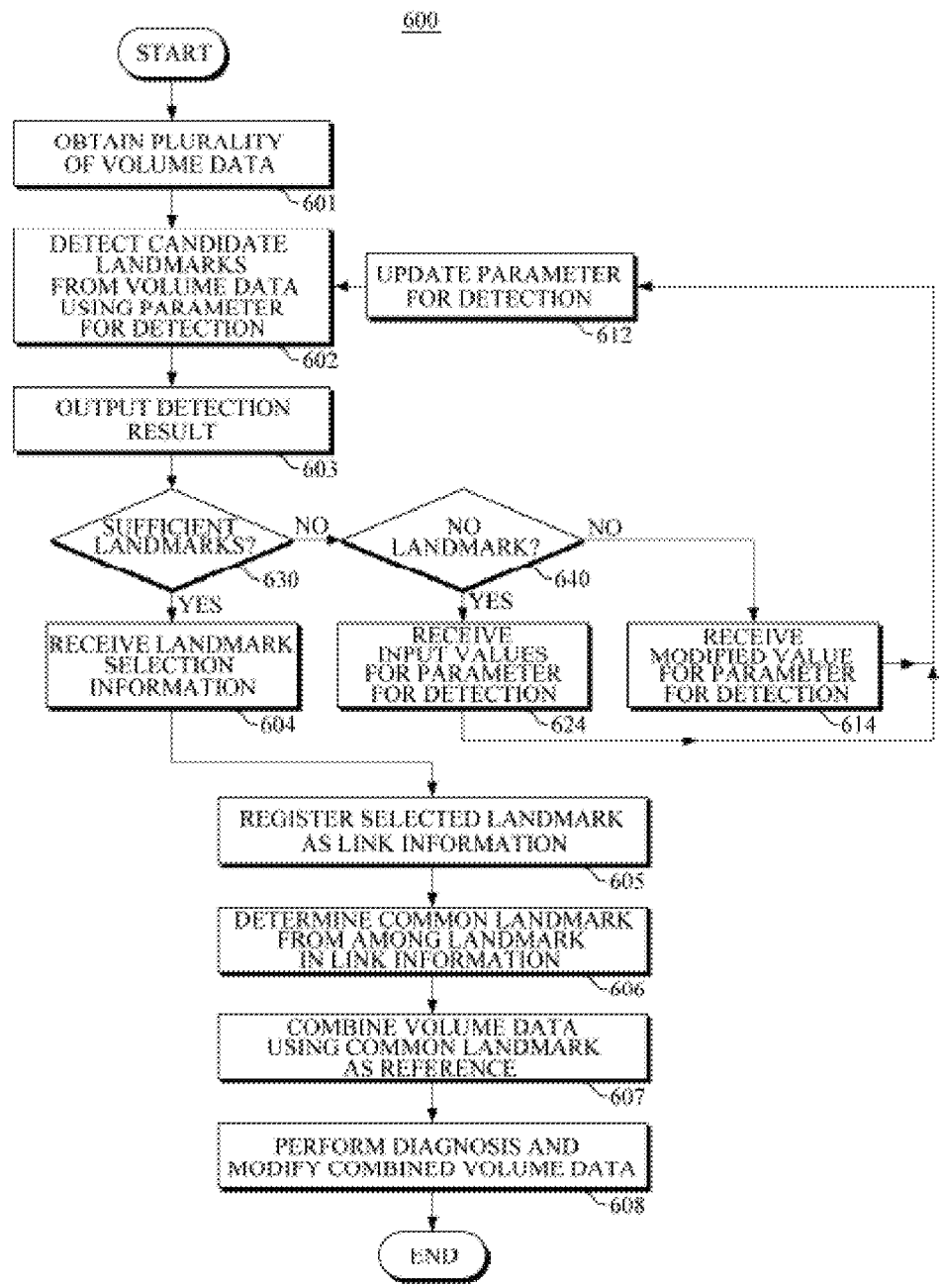
FIG. 6 is a flow chart illustrating an example of a method for combining three-dimensional ultrasound images.
Figure 7:
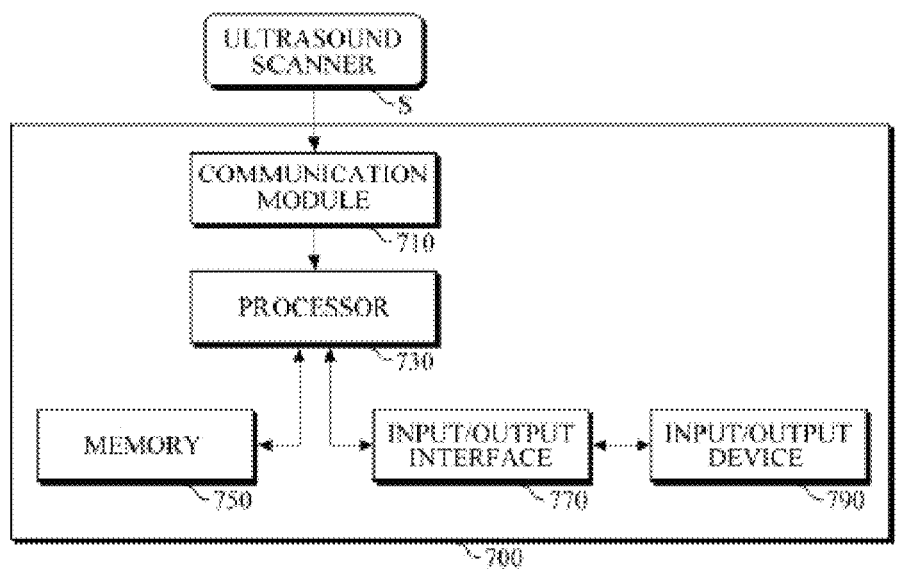
FIG. 7 is a block diagram illustrating an example of an apparatus for combining three-dimensional ultrasound images, that apparatus being capable of implementing a method for combining three-dimensional ultrasound images according to an example of the present disclosure.

Hereinafter, an example of an apparatus for combining three-dimensional (3D) ultrasound image data and an example of a method for combining 3D ultrasound image data are provided. FIG. 6 is a flow chart that illustrates an example of the method in detail. FIGS. 1 to 5 are schematic views to provide intuitive recognition of each operation of the flow chart illustrated in FIG. 6. FIG. 7 illustrates an example of an apparatus that employs a method for combining 3D ultrasound image data.

Referring to FIG. 6, a method 600 for combining 3D ultrasound image data involves operation 601 of acquiring a plurality of volume data, operation 602 of detecting one or more candidate landmarks using a parameter for detection, operation 603 of outputting a detection result, operation 604, 614 and 624 of receiving information from a user input, operation 612 of updating the parameter for detection, operation 605 of registering link information, operation 606 of determining a common landmark, operation 607 of combining the plurality of volume data, and operation 608 of diagnosing and modifying a combined volume data.

In operation 601, a plurality of volume data is obtained. The plurality of volume data divides a spatial Region of Interest (ROI) or presents the spatial ROI three-dimensionally at different locations. Herein, each piece of 'volume data' refers to a piece of 3D ultrasound image data obtained through scanning or imaging performed by a 3D ultrasound scanner.

In operation 602, in order to detect one or more candidate landmarks, diagnosis is performed on each of the obtained pieces of volume data based on a parameter for detection. In this example, a diagnosis may refer to an analysis of the data for detection of lesions or lack of lesions, or for detection of lesion like features or distinctive features such as types of tissues, vessels, nodes, bones other than a lesion.

In operation 603, the detection result is output through a monitor or a display device.

In operation 604, 614 and 624, a user checks an output detection results, and responds to the detected result in various ways. The embodiment illustrated in FIG. 6, a user is able to input information in three different ways. However, the embodiment is merely provided as an example, and aspects of the present disclosure are not limited thereto.

In operation 612, a parameter for detection is updated. The parameter for detection is used to detect one or more landmarks based on information input by the user.

In operation 605, one or more selected landmarks are each registered. The one or more selected landmarks are detected based on the information input by the user, as link information to be used for combining volume data.

In operation 606, a landmark is identified among landmarks that are commonly included in at least two pieces of volume data and are registered as link information. In addition, the identified landmark is determined as a common landmark.

In operation 607, a combined volume data is generated by combining a plurality of volume data using the common landmark.

In operation 608, diagnosis is performed on the combined volume data using a used parameter for detection, and the combined volume data is modified based on the diagnosis result.

Hereinafter, each operation of the method 600 for combining 3D ultrasound image data is described in detail.

FIG. 1 is a schematic view illustrating an example of operation 601 of obtaining a plurality of volume data that present the same spatial ROI three-dimensionally from different locations. The operation 601 may correspond to the operation 601 illustrated in FIG. 6. Each piece of volume data may be a piece of three-dimensional ultrasound image data that is obtained by using an ultrasound image diagnosis technique for the medical diagnosis of a human body's organ. In FIG. 1, heart is illustrated as an example of the organ, and an example of a procedure of obtaining volume data of the heart is illustrated. An object O of which volume data is obtained may be organs, such as fetus, breast, uterus, heart and the like. The ultrasound image diagnosis apparatus includes a scanner S in which a 3D ultrasound converter is embedded. The ultrasound image diagnosis apparatus puts the scanner S to contact with the surface of a human body, and scans by forming an ultrasound beam B of a particular frequency according to an imaging location or purpose. As a result, the ultrasound image diagnosis apparatus may obtain a plurality of volume data (V1, . . . , VN) regarding a single ROI.

Each of the plurality of volume data (V1, . . . , VN) has the same volume size, and partially overlaps with one other. In addition, each of the plurality of volume data (V1, . . . , VN) may include data of a different spatial region that other volume data do not cover. Further, each of the plurality of volume data (V1, . . . , VN) may include segmented information that describes only a part of an object, rather than the entire object, for which a consistent medical diagnosis is required. Thus, for the consistent medical diagnosis, in one example, a plurality of volume data is combined into a combined volume data regarding the same spatial ROI. By combining a plurality of volume data, which spatially segment the same spatial ROI, into an integrated combined volume data, it is possible to reduce the instances of failing to detect a lesion. On the other hand, when the diagnosis is performed on the plurality of volume data separately, some lesions may not be detected. For example, a lesion may span over more than one segment of volume data, making its detection difficult from analyzing the individual segment. The combined volume data may make it easy to compare diagnostic image data with different modalities, such as CT images and MIR images, with each other.

Figure 2:
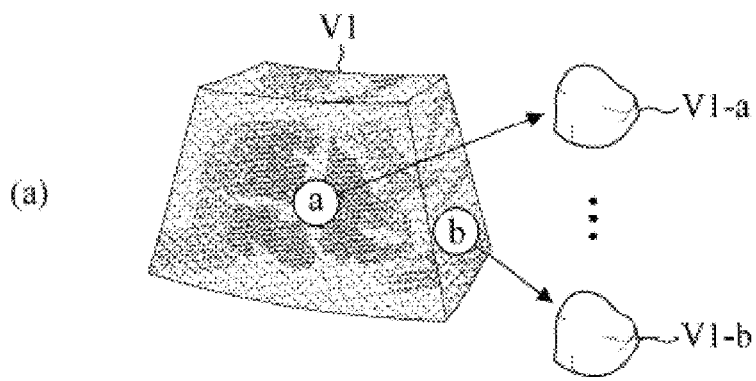
FIG. 2 is a diagram illustrating an example of an operation of extracting one or more landmarks from each three-dimensional ultrasound image in a method for combining three-dimensional ultrasound images.
Figure 2:
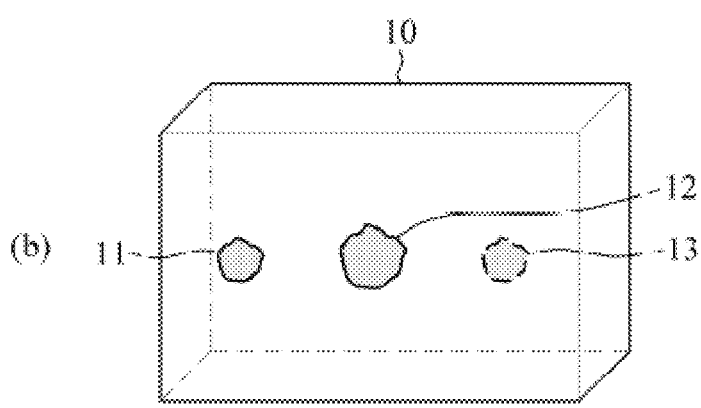

In FIG. 2, an example of operation 602 of detecting some data from each piece of volume data as a portion, that is, a landmark, is illustrated. The landmark has volume greater than a predetermined reference value and includes at least one feature distinct from the surroundings thereof. The landmark is detected using a parameter for detection.

Referring to FIG. 2, an example of a procedure of analyzing each piece of volume data and identifying a distinct portion of each piece of volume data as a landmark is illustrated. As illustrated in FIG. 2 (a), unique features may be found at the locations of VI-a and VI-b, so that the found features may be identified as a landmark VI-a and a landmark VI-b, respectively. Although FIG. 2 (a) demonstrates an example in which two landmarks are found, there is no limitation on the number of found landmarks. In some instances, no landmark may be found.

In the example illustrated in FIG. 2 (b), identified landmarks 11, 12 and 13 are displayed within volume data 10. Each of the identified landmarks 11, 12 and 13 may be identified based on identification information 110 (See FIG. 2 (c)). In other words, each landmark is associated with different identification information.

Different landmarks may belong to the same category (e.g., cyst), and each of the landmarks belonging to the same category may have different shape, size and location. Therefore, only one identical landmark exists within a piece of volume data, and it is impossible for one piece of volume data to include two or more identical landmarks.

However, a plurality of volume data may include one or more identical landmarks. A plurality of volume data including an identical landmark indicates that each of a plurality of volume data overlaps with one other at a location of the identical landmark. Therefore, it is possible to combine a plurality of volume data into a combined volume data using the identical landmark as a reference.

A 'landmark' used hereinafter refers to three-dimensional image data, which is greater than a predetermined reference value, such as 0.1 $cm^3$ or 1 $cm^3$ and composes a part of volume data including the three-dimensional image data. Properties of voxels composing the landmark are different from those of voxels in the surroundings of the landmark. Thus, the landmark and the surroundings thereof may be distinguished from each other according to voxel properties.

According to an example, a landmark may indicate a well-known lesion. A lesion may include a malignant or benign tumor, but aspects of the present disclosure are not limited thereto. In addition, according to another example, a landmark is not limited as a lesion. That is, a landmark may not be a lesion as long as it has properties that make the landmark distinct from its surroundings in the corresponding volume data. For example, a landmark may be a well-known lesion or a similar/virtual lesion designated by a user. In addition, a landmark may be a feature that can be found at a specific location in a piece of volume data and distinct from the surroundings thereof, and the feature may have nothing to do with a lesion.

A parameter for detection is reference information that is used for detecting a landmark. The parameter for detection may be a parameter that is previously stored in a storage device, such as a memory in a computer, or a parameter that is updated by a user from an existing parameter or based on a new input from a user.

A parameter for detection may be reference information that is useful for detecting a unique lesion distinct from the surroundings as a landmark. For example, the parameter may include information relating to at least one of a classification result that indicates either benignity or malignancy, category, roundness, sharpness of margin, presence of peripheral rim, echogenicity, and homogeneity of the landmark. The fact that a parameter for detection includes information relating to a classification result that indicates malignancy or benignity indicates that the parameter itself includes information indicating either benignity or malignancy or that the parameter includes more specific and analytic information regarding the classification result, such as brightness or saturation of a pixel. Such a parameter for detection may be information that is predetermined with respect to a well-known lesion.

Furthermore, a parameter for detection may be information that is useful for detecting a unique landmark that is not substantially a lesion, but something that is similar to or may be assumed to be a lesion. For example, the parameter may include link information relating to at least one of shape, texture of outer surface and orientation of the landmark. Such a parameter may be used in the event that it is difficult to detect a landmark using well-known lesion information or in the event that only few landmarks are found so that it is a challenge to combine a plurality of volume data into a combined volume data; however, aspects of the present disclosure are not limited thereto. For example, it may be understood that information relating to at least one of shape, texture of outer surface and orientation of the landmark may be used as a parameter for detection, regardless of whether a lesion exist or not.

A parameter for detection, which is used for detecting a landmark, may further include link information relating to at least one of anatomical features, such as blood vessel or bone, in addition to information relating to the lesion and/or the similar/virtual lesion. The anatomic features are information that helps improve accuracy of combination of volume data, so that the anatomic features may be utilized as a landmark or a reference for verifying the accuracy of combination.

Referring back to FIG. 6, a candidate landmark is detected by analyzing/diagnosing each piece of volume data in 602, and then a detection result is output, for example, to a display device in 603. After checking the output detection result, a user may input an appropriate response through an input device, such as a keyboard, a mouse and a touch panel, in 604, 614 or 624.

The output detection result may include various types of content. For example, the detection result may include a sufficient number of landmarks that are worth of being selected. The "sufficient number of landmarks" may indicate that there may be one or more landmarks that are worth of being used for combining volume data. In still another example, the detection result may not include a sufficient number of landmarks. In yet another example, the detection result may not include any detected landmark. In the above examples, an operation of detecting a landmark needs to be repeated using a modified or new parameter for detection, rather than using an existing parameter for detection.

According to an embodiment, a user makes a determination as to whether an output detection result includes a sufficient number of landmarks, whether an output detection result includes landmarks that are not sufficient in numbers but worth of being selected, and/or whether an output detection result does not include any landmark that is worth of being selected, if at all. In other words, a user may manually make an important determination relating to a detected landmark, which may be included in link information necessary for combining volume data. The whole process is not carried out automatically, and a part of the process is carried out manually. Thus, the above-described method for combining three-dimensional ultrasound image may be a semi-automatic method. Compared with a fully-automatic method, such a semi-automatic method needs to be performed by a more skilled person. However, it has a beneficial effect of significantly reducing reference information and calculation, which are necessary for making a determination.

Referring to FIG. 6, operation 603 of outputting a detection result is followed by operations 630 and 640 in which a user makes a determination as to the output detection result by analyzing the detection result in operation 630 and 640, and then operation of receiving a response from the user may be carried out. In FIG. 6, operations 630 and 640 of making a determination may include operation 630 of making a determination as to whether the output detection result includes a sufficient number of landmarks that are worth of being selected and operation 640 of making a determination as to whether the output detection result includes landmarks that are not sufficient in numbers but worth of being selected.

In one example, operation of receiving a response from a user corresponds to an example in which the output detection result includes a sufficient number of landmarks. In other words, it corresponds to a case in which a sufficient number of landmarks are detected by a parameter for detection during operation 602, and one or more candidate landmarks are output for a user as a detection result in operation 603. In operation 630, the user may make a determination of YES, and then select a suitable candidate landmark from among the one or more displayed candidate landmarks. Then, a response, which includes the suitable landmark selected by the user as link information, is received from the user in operation 604.

In another example, operations 614 and 624 of receiving a user response correspond to an example in which the output detection result does not include any landmark. That is, operations 614 and 624 may correspond to an event in which no landmark is detected in operation 602 or a sufficient number of landmarks is not detected in operation 602. In this event, it is necessary to modify or change the parameter for detection, which was used in operation 602. In operation 630 of making a determination as to whether the output detection result includes a sufficient number of landmarks worth of being selected, a user may make a "NO" determination, and then make a "YES" or "NO" determination in operation 640 of making a determination as to whether the output detection result includes landmarks that are not sufficient in numbers but worth of being selected. When making a "YES" determination in operation 640, the user may input a modified value to modify an existing parameter for detection. In this event, an operation of receiving a user response may be carried out as operation 614 of receiving a modified value to modify the existing parameter for detection. Alternatively, when making a "NO" determination in operation 640, the user may input a value to designate a new parameter for detection, rather than an existing parameter for detection. In this event, operation of receiving a user response may be carried out as operation 624 of receiving an input values for a new parameter for detection.

In the event that the operation of receiving a user response is performed through operation 614 of modifying an existing parameter for detection, the user may input information used to modify a parameter for detection, and the modified parameter may be used in operation 602. In this process, the parameter for detection is updated according to the user's input in operation 612. Then, in operation 602, one or more candidate landmarks are re-detected using the updated parameter, and in operation 603, the new detection result is output. Thus, operations 602 and 603 are repeated. Operation 614, 612, 602 and 603 may be performed repeatedly until a sufficient number of candidate landmarks is detected and a user selects one or more suitable landmark from among the detected candidate landmarks in operation 604.

Alternatively, in the event that operation of receiving a user response is operation 624 of receiving a new parameter for detection, the user may input information on a new parameter for detection, rather than the parameter for detection that was used in operation 602. Accordingly, the parameter for detection may be updated according to the user's input in operation 612. Then, operation 602 of re-detecting one or more candidate landmarks using the updated parameter for detection and operation of 603 of outputting the detection result may be performed repeatedly. The above-described operations may be performed repeatedly until a sufficient number of candidate landmarks is detected and a user selects one or more suitable landmarks from among the detected candidate landmarks in operation 604.

Figure 3:
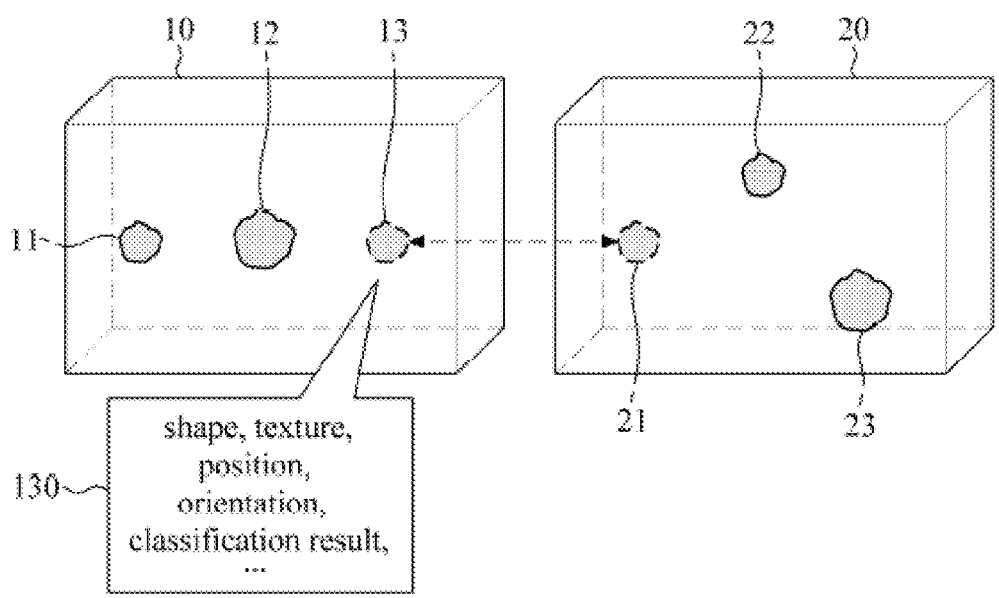
FIG. 3 is a diagram illustrating an example of an operation of discovering one common landmark from two three-dimensional ultrasound images using a well-known lesion in a method for combining three-dimensional ultrasound images.

In the event that the user selects suitable landmarks from among the output candidate landmarks in 604, the selected landmarks are associated with respective identification information 110 and 130, for example, as illustrated in FIGS. 2 and 3. The identification information 110 and 130 are ancillary data describing features of respective landmarks that are associated therewith. The identification information 110 and 130 may be used as reference information to determine whether landmarks detected from a different piece of volume data are identical to each other. In operation 605, a landmark associated with identification information may be registered as link information, which may be used when combining volume data.

After one or more landmarks are detected from each piece of volume data and registered as link information, a combined volume data is generated by connecting the volume data in 607. In this case, identification information of each of the registered landmarks is compared with that of another registered landmark, and at least two pieces of volume data that commonly include at least one of the registered landmarks, may be combined into a combined volume data using the registered landmark shared therebetween as reference.

Figure 4:
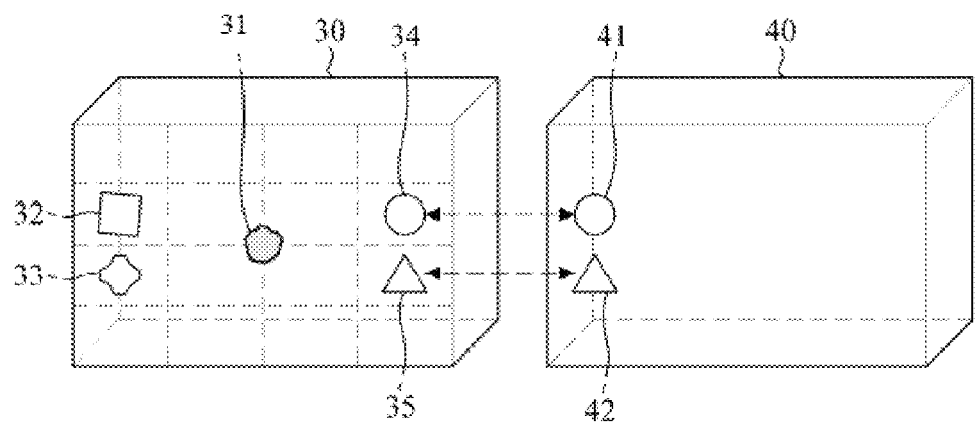
FIG. 4 is a diagram illustrating an example of an operation of extracting a common landmark from two three-dimensional ultrasound images based on a feature selected by a user, such as a similar or virtual lesion, in a method for combining three-dimensional ultrasound images.
Figure 5:
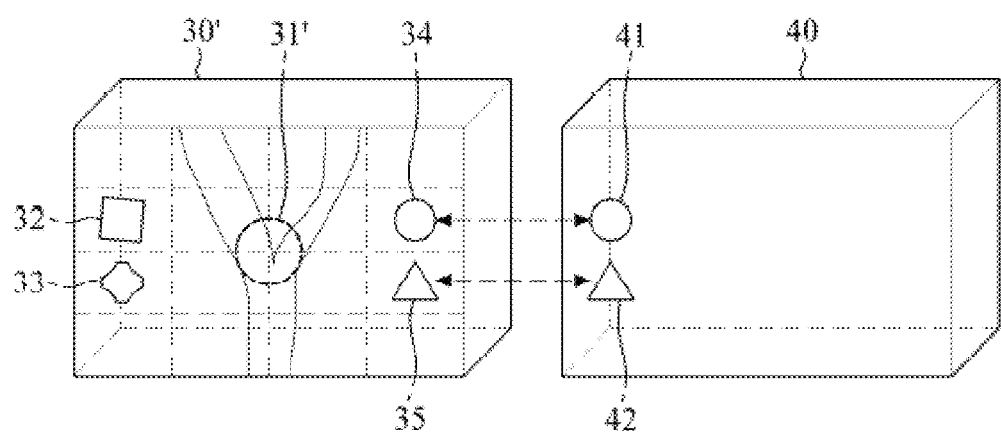
FIG. 5 is a diagram illustrating an example of an operation of extracting a common landmark from two three-dimensional ultrasound images additionally using anatomical features of the two three-dimensional ultrasound images in a method for combining three-dimensional ultrasound images.

FIGS. 3 to 5 illustrate examples of methods of connecting volume data to each other.

For example, FIG. 3 demonstrates two pieces of volume data 10 and 20. The volume data 10 includes lesions, such as tumor, as landmarks 11, 12 and 13, respectively. The volume data 20 includes lesions, such as tumor, as landmarks 21, 22 and 23. In FIG. 3, the landmark 13 that is the farthest right-side landmark of the volume data 10 and the landmark 21 that is the farthest left-side landmark of the volume data 20 are identified as the same landmark. In this example, the two pieces of volume data 10 and 20 may be combined with reference to the common landmarks 13 and 21.

In this example, whether the landmark 13 and the landmark 21 are identical to each other may be determined by comparing contents of identification information 130 that is associated with the landmarks 13 and 21. That is, whether the two landmarks are identical to each other is determined according to whether contents of identification information of one landmark are the same as those of the other landmark.

The contents of identification information may be determined in a similar way of determining the above-discussed 'parameter for detection', and may include similar contents as those of the 'parameter for detection.'

The example illustrated in FIG. 4 demonstrates two pieces of volume data 30 and 40. The volume data 30 includes one landmark 31 that is detected using lesion information as a parameter for detection. The volume data 30 includes landmarks 32, 33, 34 and 35 that are detected, not using existing lesion information, but using a parameter for detection, which is updated based on information modified or newly input by a user. The landmarks 32, 33, 34 and 35 are associated therewith respective unique identification information. Based on the identification information, the landmarks 34 and 35 may be identified to be the same as the landmarks 41 and 42 existing within the volume data 40. That is, just like the landmarks 34 and 35, the landmarks 41 and 42 are detected using the parameter for detection, which is updated based on information changed or modified by the user. Accordingly, in the example illustrated in FIG. 4, the two pieces of volume data 30 and 40 may be combined into a combined volume data using the identical landmarks 34 and 41 and the landmarks 35 and 42 as reference, wherein the landmarks 34 and 41 are identified to be identical to each other and the landmarks 35 and 42 are identified to be identical to each other.

In addition, the example illustrated in FIG. 5 demonstrates two pieces of volume data 30' and 40 that include no lesion. In the event there is no lesion, other features may be used as a landmark. For example, an anatomic feature may be used as a landmark 31', features of a similar/virtual lesion may be used as landmarks 32, 33, 34 and 35, and information on a location of an anatomical feature, such as a blood vessel and bone, may be used as a landmark. In this example, the two pieces of volume data 30' and 40 may be combined by using as reference the landmarks 34 and 41, which are identified to be identical to each other, and the landmarks 35 and 42, which are identified to be identical each other.

Then, in operation 608, diagnosis is automatically performed on the combined volume data, and the combined volume data is modified. For example, diagnosis is performed on a combined three-dimensional image data (a combined volume data) using parameters for detection, which were used for each piece of three-dimensional image data (each piece of volume data) contributing to the generation of the combined three-dimensional image data. Based on the diagnosis result, the combined three-dimensional image data may be modified.

As described above, the three-dimensional image combination technique for providing a combined image data from a plurality of three-dimensional ultrasound image data is performed by detecting a common landmark between at least two pieces of ultrasound image data, by generating a combined image data using the detected common landmark, and by helping a user to adjust a parameter used in detecting the common landmark. Accordingly, it is possible to reduce calculation necessary for combining ultrasound image data while avoiding the scenarios in which no landmark, too few landmarks or too many landmarks are extracted. Therefore, this example ensures that a combined image data will be generated from a plurality of three-dimensional ultrasound image data. In addition, diagnosis is automatically performed on the whole combined ultrasound image data using parameters that are used in generating the combined ultrasound image data, so accuracy of connecting the generated combined ultrasound image data is guaranteed. Furthermore, whether any lesion is omitted may be automatically checked as well.

The above-described examples and methods may be implemented by a software program driven by a computing device. In this case, the computing device may be an exclusive hardware device, various commercially-available standalone devices that may include desktop, laptop, notepad, tablet and smartphone, and a distributed computing system including a plurality of computing devices which operate through cooperation via a communication network. However, aspects of the present disclosure are not limited thereto. The software program includes a firmware, a module, a component, a routine, an application and the like, which are installed in a computing device to perform a designed function, but aspects of the present disclosure are not limited thereto.

As another aspect of the present disclosure, FIG. 7 demonstrates an example of an apparatus for combining three-dimensional images, which may include general components of a computing device that is capable of communication with a user.

Referring to FIG. 7, an apparatus 700 for combining three-dimensional ultrasound images includes a communication module 710, a processor 730, a memory 750, an input/output interface 770 and an input/output device 790.

The communication module 710 is a component that is used to receive a plurality of volume data from an ultrasound scanner S and configured to receive data from the ultrasound scanner S over LAN, WAN, and wireless/wired communication. Although the apparatus 700 illustrated in the example of FIG. 7 does not include the ultrasound scanner S, aspects of the present disclosure are not limited thereto such that the apparatus 700 may include the ultrasound scanner S.

The processor 730 may have the above-described method to be installed and implemented therein. For example, the processor 730 may include a microprocessor, CPU, programmable ROM, and EEPROM, but aspects of the present disclosure are not limited thereto.

The memory 750 includes a volatile/non-volatile memory and a removable/non-removable medium. The memory 750 may store an instruction that embodies a software program which implements the above-described method, as well as a parameter for detection, a landmark generated in response to the implementation, and identification information associated with the landmark. The memory 750 may be a non-transitory storage medium, the examples of which include floppy disk, hard disk, solid disk, optical disk, CD, DVD, USB, flash memory, magnetic disk, and magnetic tape; however, aspects of the present disclosure are not limited thereto.

The input/output device 790 may include an input device by which a user inputs an instruction or information to the processor 730 through the input/output interface 770 of the apparatus 700. An output device that uses the processor 770 outputs information to a user through the input/output interface 770. For example, the input/output device 790 may include a monitor, a display unit, a touch panel, a screen, a speaker, a keyboard, a keypad, a pointing device including a mouse, and a microphone. In one example, the input/output device 790 is a touch panel that outputs information to a user and allows a user to input an instruction. However, aspects of the present disclosure are not limited thereto.

According to an example, the apparatus 700 may include a computer readable medium that stores instructions that are executable in a computer. The 'computer readable medium' may include a storage medium configured to store an instruction and a signal medium for communication.

The storage medium may include the memory 750, a cache memory embedded in the processor 730 of FIG. 7, a volatile/non-volatile memory, and a removable/non-removable medium. The signal medium for communication is a medium composed of modulated signals, such as carrier signal, and may include a signal which a computing device uses over wired/wireless communication within a local entity or at a remote entity.

The methods and/or operations described above may be recorded, stored, or fixed in one or more non-transitory computer-readable storage media that includes program instructions to be implemented by a computer to cause a processor to execute or perform the program instructions. The media may also include, alone or in combination with the program instructions, data files, data structures, and the like. A non-transitory computer-readable storage medium may be any data storage device that is capable of storing the software or instructions and any associated data, data files, and data structures so that they can be read by a computer system or processing device. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, or any other non-transitory computer-readable storage medium known to one of ordinary skill in the art. Examples of program instructions include machine code, such as produced by a compiler, and files containing higher level code that may be executed by the computer using an interpreter. The described hardware devices may be configured to act as one or more software modules in order to perform the operations and methods described above, or vice versa. In addition, a computer-readable storage medium may be distributed among computer systems connected through a network and computer-readable codes or program instructions may be stored and executed in a decentralized manner. Also, functional programs, codes and code segments to implement those embodiments may be easily inferred by programmers who are skilled in the related art.

The various units, modules and methods described above may be implemented using one or more hardware components, one or more software components, or a combination of one or more hardware components and one or more software components. A hardware component may be, for example, a physical device that physically performs one or more operations, but is not limited thereto. Examples of hardware components include microphones, amplifiers, low-pass filters, high-pass filters, band-pass filters, analog-to-digital converters, digital-to-analog converters, and processing devices.

A software component may be implemented, for example, by a processing device controlled by software or instructions to perform one or more operations, but is not limited thereto. A computer, a computing device, controller, or other control device may cause the processing device to run the software or execute the instructions. One software component may be implemented by one processing device, or two or more software components may be implemented by one processing device, or one software component may be implemented by two or more processing devices, or two or more software components may be implemented by two or more processing devices.

A processing device may be implemented using one or more general-purpose or special-purpose computers, such as, for example, a processor, a controller and an arithmetic logic unit, a digital signal processor, a microcomputer, a field-programmable array, a programmable logic unit, a microprocessor, or any other device capable of running software or executing instructions. The processing device may run an operating system (OS), and may run one or more software applications that operate under the OS. The processing device may access, store, manipulate, process, and create data when running the software or executing the instructions. For simplicity, the singular term "processing device" may be used in the description, but one of ordinary skill in the art will appreciate that a processing device may include multiple processing elements and multiple types of processing elements. For example, a processing device may include one or more processors, or one or more processors and one or more controllers. In addition, different processing configurations are possible, such as parallel processors or multi-core processors.

A processing device configured to implement a software component to perform an operation A may include a processor programmed to run software or execute instructions to control the processor to perform operation A. In addition, a processing device configured to implement a software component to perform an operation A, an operation B, and an operation C may have various configurations, such as, for example, a processor configured to implement a software component to perform operations A, B, and C; a first processor configured to implement a software component to perform operation A, and a second processor configured to implement a software component to perform operations B and C; a first processor configured to implement a software component to perform operations A and B, and a second processor configured to implement a software component to perform operation C; a first processor configured to implement a software component to perform operation A, a second processor configured to implement a software component to perform operation B, and a third processor configured to implement a software component to perform operation C; a first processor configured to implement a software component to perform operations A, B, and C, and a second processor configured to implement a software component to perform operations A, B, and C, or any other configuration of one or more processors each implementing one or more of operations A, B, and C. Although these examples refer to three operations A, B, C, the number of operations that may implemented is not limited to three, but may be any number of operations required to achieve a desired result or perform a desired task.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A method for combining three-dimensional ultrasound image data, comprising:
   obtaining a plurality of three-dimensional ultrasound image data that is associated with a Region of Interest (ROI);
   detecting one or more landmarks in each of the plurality of three-dimensional ultrasound image data using a parameter associated with the one or more landmarks, the one or more landmarks comprising a feature distinct from surroundings of the one or more landmarks;
   outputting the detected one or more landmarks;
   receiving a user input, the user input selecting at least one landmark among the detected one or more landmarks or changing the parameter associated with the one or more landmark according to a number of the detected one or more landmarks;
   in response to receiving the user input changing the parameter, updating the parameter based on a changed parameter, and repeating the detecting, the outputting, and the receiving based on the updated parameter; and
   in response to receiving the user input selecting the at least one landmark, generating a combined three dimensional ultrasound image, by combining two pieces of the plurality of three-dimensional ultrasound image data using at least one landmark which is commonly included in the two pieces among the selected at least one landmark.

2. The method of claim 1, wherein the plurality of three-dimensional ultrasound image data overlaps with one another and correspond to different locations of the ROI, and wherein the detecting comprises:
   performing diagnosis on each of the plurality of three-dimensional ultrasound image data using the parameter; and
   detecting the one or more landmarks based on the diagnosis, the one or more landmarks having volume greater than a predetermined reference value.

3. The method of claim 1, further comprising:
   performing diagnosis on the combined three-dimensional ultrasound image using the parameter; and
   modifying the combined three-dimensional image based on the performed diagnosis.

4. The method of claim 1, wherein outputting the detected one or more landmarks comprise outputting candidate landmarks as a detection result, and waiting to receive the user input.

5. The method of claim 1, wherein receiving the user input changing the parameter comprises receiving the user input modifying the parameter associated with the one or more landmark when the number of the detected one or more landmarks is not a sufficient number to select the at least one landmark.

6. The method of claim 1, wherein the receiving the user input changing the parameter comprise receiving the user input inputting a new parameter associated with the one or more landmarks when the one or more landmarks are not detected.

7. The method of claim 1, wherein the parameter comprises at one of a classification result which indicates either benignity or malignancy, category, roundness, sharpness of margin, presence of peripheral rim, echogenicity, and homogeneity.

8. The method of claim 1, wherein the parameter comprises information that relates to one of an entire shape, texture of an outer surface and posture.

9. The method of claim 7, wherein the parameter further comprises link information that relates to one of anatomical features, such as a blood vessel and bone, which are located close to a landmark.

10. An apparatus for combining three-dimensional ultrasound image data, the apparatus comprising:
    an input/output device; and
    a processor configured to:
        obtain a plurality of three-dimensional ultrasound image data that is associated with a Region of Interest (ROI);
        detect one or more landmarks in each of the plurality of three-dimensional ultrasound image data using a parameter associated with the one or more landmarks, the one or more landmarks comprising a feature distinct from surroundings of the one or more landmarks;
        output the detected one or more landmarks through the input/output device;
        receive a user input, the user input selecting at least one landmark among the detected one or more landmarks or changing the parameter associated with the one or more landmark according to a number of the detected one or more landmarks;
        in response to receiving the user input changing the parameter, update the parameter based on a changed parameter, and repeat the detecting, the outputting, and the receiving based on the updated parameter; and
        in response to receiving the user input selecting the at least one landmark, generate a combined three dimensional ultrasound image, by combining two pieces of the plurality of three-dimensional ultrasound image data using at least one landmark which is commonly included in the two pieces among the selected at least one landmark.

11. The apparatus of claim 10, wherein the plurality of three-dimensional ultrasound image data partially overlap with one another and correspond to different locations of the ROI, and
    wherein the processor is configured to perform diagnosis on each of the plurality of the three-dimensional ultrasound image data using the parameter and detect the one or more landmarks based on the diagnosis, the landmark having volume greater than a predetermined reference value.

12. The apparatus of claim 10, wherein the processor is further configured to perform diagnosis on the combined three-dimensional ultrasound image using the parameter and modify the combined three-dimensional image based on the performed diagnosis.

13. The apparatus of claim 10, wherein the processor is configured to control input/output device to output candidate landmarks as a detection result, and wait to receive the user input.

14. The apparatus of claim 10, wherein the processor is configured to receive the user input modifying the parameter associated with the one or more landmark when the number of the detected one or more landmarks is not a sufficient number to select the at least one landmark.

15. The apparatus of claim 10, wherein the processor is configured to receive the user input inputting a new parameter associated with the one or more landmarks when the one or more landmarks are not detected.

16. The apparatus of claim 10, wherein the parameter comprises information relating to one of a classification result that indicates either benignity or malignancy, category, roundness, sharpness of margin, presence of peripheral rim, echogenicity, and homogeneity.

17. The apparatus of claim 10, wherein the parameter comprises one of shape, texture of outer surface and orientation.

18. The apparatus of claim 16, wherein the parameter further comprises link information relating to one of anatomical features, such as blood vessel and bone, which are close to the landmark.

19. A non-transitory computer readable hardware medium storing instructions configured to cause a computing device to perform the method of claim 1.

20. The apparatus of claim 10, wherein the input/output device is configured to output whether the output detection result includes a sufficient number of landmarks, whether an output detection result includes landmarks that are not sufficient in numbers but worthy of being selected, and whether an output detection result does not include any landmark worthy of being selected.

* * * * *